US009138317B2

(12) United States Patent
McGee (10) Patent No.: US 9,138,317 B2
(45) Date of Patent: Sep. 22, 2015

(54) CONDUITS FOR ENHANCING TISSUE REGENERATION

(71) Applicant: Thomas D. McGee, Ames, IA (US)

(72) Inventor: Thomas D. McGee, Ames, IA (US)

(73) Assignee: Osteoceramics, Inc, Ames, IA (US)

( * ) Notice: Subject to any disclaimer, the term of this patent is extended or adjusted under 35 U.S.C. 154(b) by 0 days.

(21) Appl. No.: 13/803,606

(22) Filed: Mar. 14, 2013

(65) Prior Publication Data

US 2014/0276640 A1 Sep. 18, 2014

(51) Int. Cl.
| | | |
|---|---|---|
| *A61F 2/02* | (2006.01) | |
| *A61F 2/28* | (2006.01) | |
| *A61B 17/56* | (2006.01) | |
| *A61M 27/00* | (2006.01) | |
| *A61B 17/80* | (2006.01) | |
| *A61B 17/74* | (2006.01) | |

(52) U.S. Cl.
CPC . *A61F 2/28* (2013.01); *A61B 17/56* (2013.01); *A61B 17/74* (2013.01); *A61B 17/8095* (2013.01); *A61M 27/002* (2013.01)

(58) Field of Classification Search
None
See application file for complete search history.

(56) References Cited

U.S. PATENT DOCUMENTS

| | | | |
|---|---|---|---|
| 3,787,900 | A | 1/1974 | McGee |
| 5,019,087 | A | 5/1991 | Nichols |
| 5,645,591 | A | 7/1997 | Kuberasampath |
| 6,174,333 | B1 | 1/2001 | Kadiyala |
| 6,206,931 | B1 | 3/2001 | Cook et al. |
| 6,217,620 | B1 | 4/2001 | Park |
| 6,280,473 | B1 | 8/2001 | Lemperle |
| 6,312,467 | B1 | 11/2001 | McGee |
| 6,364,909 | B1 | 4/2002 | McGee |
| 6,716,225 | B2 | 4/2004 | Li et al. |
| 6,719,793 | B2 | 4/2004 | McGee |
| 7,299,805 | B2 | 11/2007 | Bonutti |
| 7,722,678 | B2 | 5/2010 | Brown |
| 8,038,708 | B2 | 10/2011 | Case et al. |
| 8,546,456 | B2 | 10/2013 | Rose |
| 2005/0214340 | A1 | 9/2005 | Erbe |
| 2009/0143867 | A1 | 6/2009 | Gage |
| 2009/0182336 | A1 | 7/2009 | Brenzel |
| 2011/0087227 | A1 | 4/2011 | Mazur |
| 2011/0190907 | A1 | 8/2011 | Porter |

FOREIGN PATENT DOCUMENTS

| | | |
|---|---|---|
| DE | 10201052914 | 5/2012 |
| EP | 0896744 | 2/1999 |

OTHER PUBLICATIONS

C.E. Olson, T.D. McGee, Dr. W. D. Hoefle and Dr. R. Kudej, Osteoceramic Bone Replacement and Grafting, Ceramic Trans., 2000, vol. 101, 187-201.
C.E. Olson, S.D. Wagner and T.D, McGee, Guided Diaphysis Regeneration, Biomaterials in Orthopedics, M.J. Yazemski (ed.), chapter 9, 2004, pp. 195-212, Marcel Dekker, New York.
Sergey V. Dorozhkin, Biomaterials: Bioceramics of calcium orthophosphates, Science Direct—www.sciencedirect.com, Iowa State University Library, Jan. 1, 2010, pp. 1-51.
S.K. Nandi, S. Roy, P. Mukherjee, B. Kundu, D.K. De and D. Basu, Orthopaedic applications of bone graft & graft substitutes: a review, Indian J. Med. Res. 132, Jul. 2010, pp. 15-30.
Mohamed Attawia, Sudha Kadiyala, Kim Fitzgerald, Karl Kraus and Scott P. Bruder, Cell-Based Approaches for Bone Graft Substitutes, Bone Graft Substitutes, Cato T. Laurencin, ed., 2003, ASTM International, Chapter 7, pp. 136-141.
A. Seth Greenwald, Soctt D. Boden, Robert L. Barrack, Mathias P.G. Bostrom, Victor M. Goldberg, M.J. Yaszemski, Christine S. Heim, The Evolving Role of Bone-Graft Substitutes, Orthopaedic Device Forum, American Academy of Orthopaedic Surgeons, 2010.
G.G. Niederauer, T.D. McGee, J.C. Keller and R.S. Zacharias, Attachment of epithelial cells and fibroblasts to ceramic materials, Biomaterials, 1994, vol. 15, No. 5, pp. 342-351.
John C. Keller, Jeanine G. Collins, Gabrielle G. Niederauer and Thomas D. McGee, In vitro attachment of osteoblast-like cells to osteoceramic materials, Dental Materials, Jan. 1997, vol. 13, pp. 62-68.
Joon Park and R.S. Lakes, Biomaterials, Springer, 2007, Section 10.1 (cited in patent application, Conduits for Tissue Regeration application).
Guodong Song, Pamela Habibovic, Chongyun Bao, Jing Hu, Clemens A Van Blitterswijk, Huipin Yuan, Wenchuan Chen and Hockin H.K. Xu, The homing of bone marrow MSCs to non-osseous sites for ectopic bone formation induced by osteoinductive calcium phosphate, National Institutes of Health Public Access Author Manuscript, 2013.
Aaron Nauth, Erica Giles, Benjamin K. Potter, Leon J. Nesti, Frederick P. O'Brien, Michael Bosse, Jeffrey O. Anglen, Samir Mehta, Jaimo Ahn, Theodore Miclau and Emil Schemitsch, Heterotopic Ossification in Orthopaedic Trauma, J Orthop. Trauma 26(12), 2012, pp. 684-688.
Thomas A. Davis, Yelena Lazdun, Benjamin K. Potter, Jonathan A. Fosberg, Ectopic Bone Formation in Severely-Injured Orthopaedic Patients—A Hematopoietic Niche, Bone 56, 2013, pp. 119-126.
Emilie V. Cheung, Dhirendra S. Katti, Randy N. Rosier and Cato T. Laurencin, Review of State of the Art: Growth Factor-Based Systems of Use as Bone Graft Substitutes, Bone Graft Substitutes, Cato T. Laurencin, ed., 2003, ASTM International, Chapter 10, pp. 174-193.

*Primary Examiner* — Mina Haghighatian
(74) *Attorney, Agent, or Firm* — Ryan N. Carter (57) ABSTRACT

Apparatuses, systems, and methods for enhancing bone or soft tissue regeneration are provided. For example, a conduit, having one or more segments, can originate at a tissue regeneration site and can have a first opening to promote physiological signals to enter the conduit and transit to a second opening that penetrates a histologically rich source of multipotent mesenchymal cells, promoting the multipotent mesenchymal cells to produce tissue regeneration response products, the response products transiting through the second opening to egress at the first opening of the conduit, and promoting tissue regeneration at the tissue regeneration site. Transit of the physiological signals and the tissue regeneration response products is promoted through physical and/or chemical means, as is promotion of the anatomical functionality of the regenerated tissue. For example, a number of the segments of the conduit can be formed at least partially from an osteoceramic material.

39 Claims, 6 Drawing Sheets

Fig. 1A

SOFT TISSUE WOUND HEALING SEQUENCE. REPRINTED WITH PERMISSION FROM HENCH AND ERTHRIDGE (1975). COPYRIGHT © 1975, WILEY INTERSCIENCE. (MODIFIED FOR CLARITY IN THIS APPLICATION.)

Fig. 1B

SEQUENCE OF EVENTS FOLLOWED BY BONE FRACTURE. REPRINTED BY PERMISSION FROM HENCH AND ETHRIDGE (1975). COPYRIGHT © 1975 WILEY INTERSCIENCE. (SLIGHTLY MODIFIED FOR CLARITY IN THIS APPLICATION.)

Fig. 1C
DRAWING OF THE LONGITUDINAL SECTION OF A FRACTURED RIB OF A RABBIT AFTER TWO WEEKS (H & E STAIN) REPRINTED WITH PERMISSION FROM HAM AND HARRIS (1971) COPYRIGHT © 1971. ACADEMIC PRESS
(BOUNDARY LINES ADDED FOR CLARITY IN THIS APPLICATION.)

CONDUITS FOR ENHANCING TISSUE REGENERATION

BACKGROUND

During orthopedic surgery, a soft tissue wound must be made to gain access to the bones to be repaired and a bone wound is present from the original defect and from the process of treating the bone. Both types of wounds cause tissue responses that are well characterized but not well understood. Park and Lakes describe these processes in their *Biomaterials* book, Vol. 3, as follows, with the figure numbers being revised for consistency with the present patent application:

10-1. Normal Wound-Healing Processes 10.1.1. Inflammation

Whenever tissues are injured or destroyed, the adjacent cells respond to repair them. An immediate response to any injury is the inflammatory reaction. Soon after injury, constriction of capillaries occurs (stopping blood leakage); then dilation. Simultaneously there is greatly increased activity in the endothelial cells lining the capillaries. The capillaries become covered by adjacent leukocytes, erythrocytes, and platelets (formed elements of blood). Concurrently with vasodilation, leakage of plasma from capillaries occurs. The leaked fluid combined with the migrating leukocytes and dead tissue will constitute exudate. When enough cells are accumulated by lysis, the exudate becomes pus. It is important to know that pus can sometimes occur in nonbacterial (aseptic) inflammation.

At the time of damage to the capillaries, the local lymphatics are also damaged since they are more fragile than the capillaries. However, the leakage of fluids from capillaries will provide fibrinogen and other formed elements of the blood, which will quickly plug the damaged lymphatics, thus localizing the inflammatory reaction.

All of the reactions mentioned above—vasodilation of capillaries, leakage of fluid into the extravascular space, and plugging of lymphatics—will provide the classic inflammatory signs: redness, swelling, and heat, which can lead to local pain. • • •

10.1.2 Cellular Response to Repair

Soon after injury the mesenchymal cells evolve into migratory fibroblasts that move into the injured site while the necrotic debris, blood clots, etc. are removed by the granulocytes and macrophages. The inflammatory exudate contains fibrinogen, which is converted into fibrin by enzymes released through blood and tissue cells. The fibrin scaffolds the injured site. The migrating fibroblasts use the fibrin scaffold as a framework onto which the collagen is deposited. New capillaries are formed following the migration of fibroblasts, and the fibrin scaffold is removed by the fibrinolytic enzymes activated by the endothelial cells. The endothelial cells, together with the fibroblasts, liberate collagenase, which limits the collagen content of the wound.

After 2 to 4 weeks of fibroblastic activities, the wound undergoes remodeling, during which the glycoprotein and polysaccharide content of the scar tissue decreases and the number of synthesizing fibroblasts also decreases. A new balance of collagen synthesis and dissolution is reached, and the maturation phase of the wound begins. The time required for the wound-healing process varies for various tissues, although the basic steps described here can be applied in all connective tissue wound-healing processes.

Figure 1A:
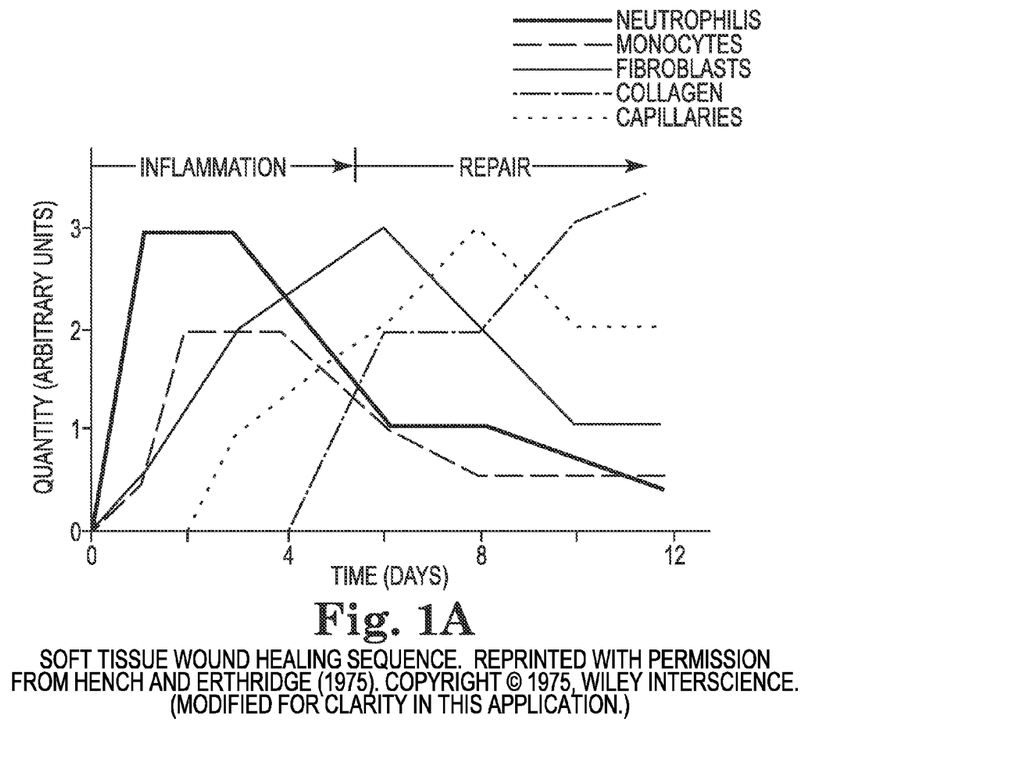
FIGS. 1A-1C illustrate examples of soft tissue and hard tissue repair in accordance with the present disclosure.

The healing of soft tissues—especially the healing of skin wounds—has been studied intensively since this is germane to all surgery. The degree of healing can be determined by histochemical or physical parameters. A combined method will give a better understanding of the wound healing process. FIG. 1A shows a schematic diagram of sequential events of the cellular response of soft tissues after injury. • • •

Figure 1B:
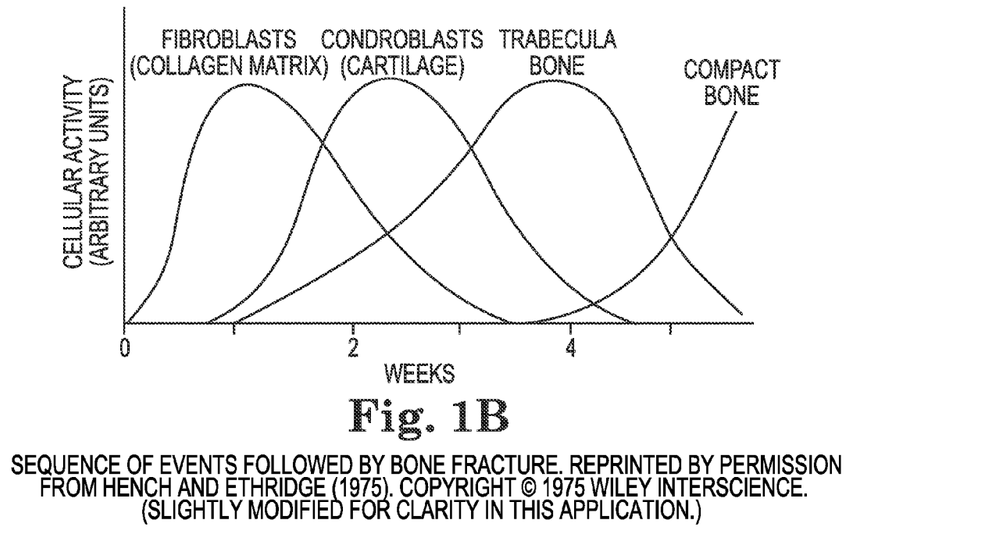

The healing of bone fracture is regenerative rather than simple repair. The only other tissue that truly regenerates in humans is liver. However, the extent of regeneration is limited in humans. The cellular events following fracture of bone are illustrated in FIG. 1B.

When a bone is fractured, many blood vessels (including those in the adjacent soft tissues) hemorrhage and form a blood clot around the fracture site. Shortly after fracture the fibroblasts in outer layer of the periosteum and the osteogenic cells in the inner layer of the periosteum migrate and proliferate toward the injured site. These cells lay down a fibrous collagen matrix called a callus. Osteoblasts evolved from the osteogenic cells near the bone surfaces start to calcify the callus into trabeculae, which are the structural elements of spongy bone. The osteogenic cells migrating further away from an established blood supply become chondroblasts, which lay down cartilage. Thus, after 2 to 4 weeks the periosteal callus is made of three parts, as shown in FIG. 1C.

Simultaneous with external callus formation, a similar repair process occurs in the marrow cavity. Since there is an abundant supply of blood, the cavity turns into callus rather quickly and becomes fibrous or spongy bone.

New trabeculae develop in the fracture site by appositional growth, and the spongy bone turns into compact bone. This maturation process begins after about 4 weeks.

Figure 1C:
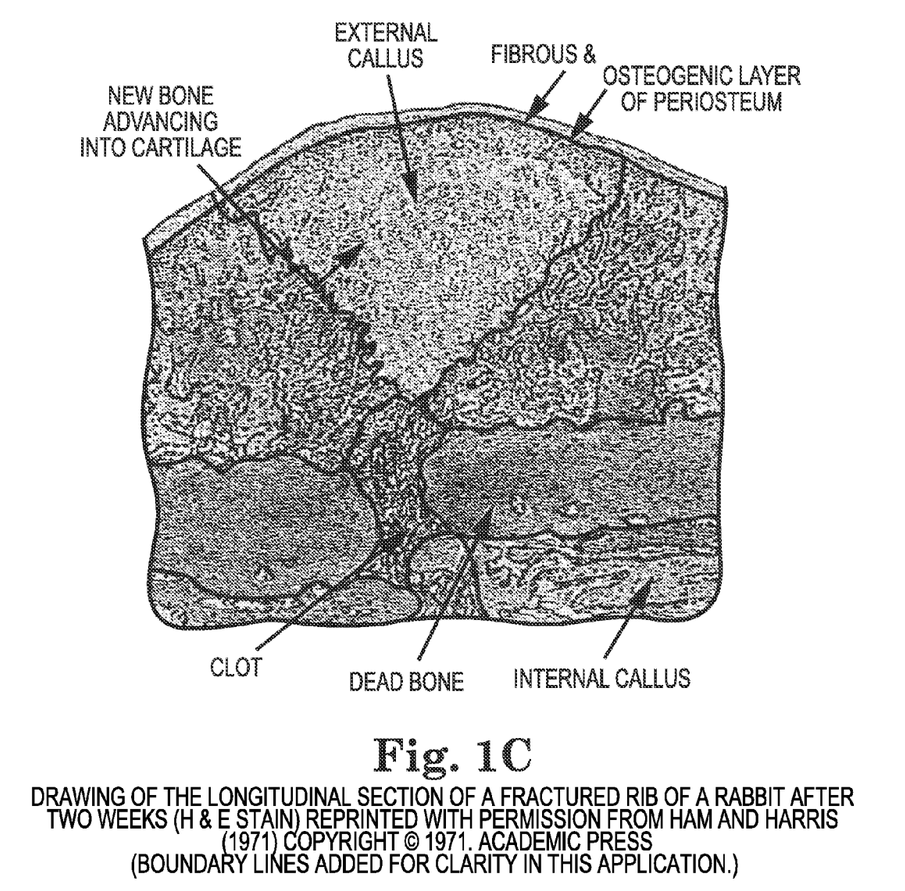

From the above citation, note that in this widely accepted model by Parks and Lakes, the callus shown in FIG. 1C is massive compared to the thickness of the original, now dead, cortical bone shown at the bottom of the figure. This massive callus is necessary because the fibrin and chondroital structure is much weaker than the dense cortical bone.

The formation of new bone follows a well-known sequence. First, osteoclasts remove necrotic tissue. Then, osteoblasts lay down a collagenous matrix of a specific shape. After the soft tissue's basic form is complete, mineralization of the bone occurs to develop the final properties. Prior formation of the soft tissue is inherent in bone formation.

The dominant mineral in bone is an impure hydroxyapatite, commonly denoted $Ca_{10}(PO_4)_6(OH)_2$, with a Ca:P ratio of about 1.62:1, instead of 1.67 as indicated in the chemical formula. Experimentally, calcium phosphates with a Ca:P ratio between 1:1 and 2:1 are not walled off by a tissue foreign body response. For this reason, scientists have studied calcium phosphate for bone repair. A recent review by S. V. Dorozhkin, 2009, cited 382 scientific papers in which various calcium phosphate formulations were studied for use in bone repair. He concluded that formulations based upon calcium phosphates do not have sufficient strength for bone graft applications.

Advancements have been made in the use of calcium phosphates in situations where non-load-bearing bone regeneration is enhanced. However, calcium phosphates themselves have not been successfully used in load-bearing graft applications. This is in agreement with the 1974 U.S. Pat. No. 3,787,900 by McGee that showed that a second inert phase is needed to obtain enduring strength. The content of U.S. Pat. No. 3,787,900, McGee, issued Jan. 29, 1974, is incorporated by reference into this application.

Artificial Bone Grafts:

McGee is the only inventor that has succeeded in making artificial bone grafts that are functional under load. He used the geometry of what was labeled the "osteoceramic" bone graft to allow the bone to develop strength for torsional, tensile, compressive, and bending loads, and to ensure a blood supply to augment bone attachment to the implant. Research has been conducted to attempt to find other load-bearing artificial bone grafts. These are often identified as Bone Graft Substitutes. An excellent review of the state of the art of bone graft substitutes is given in *Bone Graft Substitutes*, CT Laurencin, Ed., (2003) written by a committee from ASTM International in conjunction with THE AMERICAN ACADEMY OF ORTHOPEDIC SURGEONS. Thirty-five experts provide the clinical, scientific, and practical aspects of bone graft substitutes in 17 chapters. The preface has an explanation that the state of the art is for Bone Void Fillers, not for bone graft substitutes. This research can be subdivided into two categories: Tissue Engineering and Bone Void Fillers because they have different theoretical bases. The contents of this book constitute a basis for the state of the prior art.

Tissue Engineering:

Tissue Engineering is a term applied to attempts to use artificial materials or systems to invoke the tissue to repair itself in situations where it normally will not do so. The initial effort was to use bulk calcium phosphates, but that failed because the calcium phosphate compounds are too weak. It is quite clear that dense calcium phosphates are unsuitable for load-bearing replacement of functional bone. Subsequently, tissue engineering evolved to support a theoretical approach, usually requiring three components that may have different names assigned to them by different authorities. The three are a source of osteogenic cells, a scaffold on which the cells can be grown, and a source of stimulants to control and enhance the proliferation and differentiation of osteogenic cells. The usual osteogenic cells are osteoblasts that are harvested from the patient and grown in cultures in vitro. The components are cultured together in vitro until bone is well developed on the scaffold. Then the implant is placed in a bony defect with the expectation that it will be replaced with new bone by the adjacent tissue, becoming strong enough to be functional. In load-bearing bone this expectation has not been fulfilled. A second expectation is that the entire assembly will be absorbed by the adjacent bone and replacement bone will appear at the rate the implant is absorbed. This, too, has not been fulfilled.

Although the bone generation process is very complex, only osteoblast cells have been studied extensively to try to induce bone to form. This approach neglects the function of other cells, enzymes, and mechanisms that participate. This is a serious flaw in the theory. Glowing reports of success have been claimed in scientific reports. The best results have been where the patient's own osteoblast cells have been cultured in vitro on a scaffold of porous calcium phosphate together with growth factors or other bone stimulants. New bone has formed on the scaffolds, but it has not been strong load-bearing bone. Ten times the concentration of cells is required than is necessary for natural bone generation processes. Porous calcium phosphate structures with large surface areas are inherently weak. The new bone is too disorganized to fit the structure and is structurally weak. It is necessary for that structure and the new bone to be replaced by cortical bone before it can function under load. Tissue engineering has not yet achieved functional bone under load-bearing conditions.

Bone Void Fillers:

Bone void fillers are in commercial use in current orthopedic surgery. They are widely used as osteoinductive aids in many applications, especially in fusion of vertebrae, oral surgery, and periodontics. The osteoinductive nature of Demineralized Bone Matrix (DBM) was discovered in 1965 by M R Urist who found it induced ectopic bone formation in rat muscle. He postulated that specific proteins within the DBM were responsible for the activity and classified them as Bone Morphogenic Proteins (BMP). After animal experiments, the first use in humans occurred in 1975 when B. M. Libin, H. L. Ward and L. Fishman used lyophilized allograft DBM particles to treat periodontal defects. BMP was found most suitable for applications where it was contained in some way, because uncontained particles would migrate. In 1983, Urist extracted BMP from the insoluble cross-linked collagen in DBM. In 1988, J M Wozney, et al., identified the generic sequences of BMP and identified important components, BMP-1 to BMP-15. BMP-1 is not a growth factor. BMP-8 is important to muscle formation. Mixtures of MBP-2 and BMP-7, also known as osteogenic protein 1 (OP-1), have been exploited in commercial products, often combined with DBM and/or a collagen carrier.

The use of these BMP in humans is restricted by the FDA to void filling applications where they supplement the use of marrow, blood and cancellous bones harvested from the patient to enhance the kinetics of bone regeneration and where fixation of the bones in position is accomplished by other means. They are no better than the autologous sources. Many variations in composition and carriers are available. They often include Transformation Growth Factors (TGFs), which are very complex. More than 100 TGFs have been identified. TGFs are believed to attach to active sites on the surface of cells and their functions can be reversed by the presence of other growth factors. Many of the necessary features of tissue formation are still unknown. Scientific advances in this phase of tissue engineering have been achieved in recent years but much more research is needed. When used without bone grafts to support the void area, in the words of a spinal surgeon, "They just squish out."

BRIEF DESCRIPTION OF THE DISCLOSURE

Example of Need:

An example of the need for ways to treat orthopedic medical problems is the horrific nature of the injuries received in combat from improvised explosive devices. When these massive devices explode in close proximity to personnel, they produce explosions of such force that pieces of armor may become shrapnel to cause serious local injuries, and the force of the explosion may blow the soft tissue off of the bones. Often the injury is so severe that parts of extremities must be amputated. This may leave insufficient bone for prosthesis attachment. If artificial bone grafts were available, or if bone repair or elongation could be induced, less amputation might be required or extensions for prosthesis attachment might be possible. Clearly there are many other trauma situations that could benefit. There is an urgent need for enhancing regeneration of, for example, functional load-bearing bone.

Deficiencies in the Present Art:

The present state of the art has not developed ways to enhance the functions supporting both soft tissue healing and bone healing needed for natural wound healing and bone regeneration. Excessive time is often needed currently to obtain functional bone with or without medical intervention. Often functional bone cannot be achieved. There is an urgent need for more rapid, efficient, and strong bone recovery. This is also true for soft tissue applications where organs, muscles, nerves, connective tissues, and many other components need access to multipotent mesenchymal cells, such as found, for example, in the umbilical cords of newborns.

The present state of the art is based on tissue engineering in which cells are harvested from a patient, cultured in appropriate media to increase their number, and returned to the patient. The type of cells is very limited, often to only one type, such as the osteoblast for orthopedic repair. In that case, the scaffold on which the cells are deposited is usually highly porous calcium phosphate that is too weak to support mechanical loads inherent in the tissue repair site. Kinetic stimulants, such as DBM and growth factors, are often included, but access to mesenchymal cells is not provided. In the case of nerve wound repair, a sheath at the wound site is often termed a conduit, but its purpose is to confine the grafting materials, not to utilize mesenchymal cells.

The Conduit of the Present Disclosure:

The present disclosure describes using a conduit as an elongated, hollow, protective enclosure that enables transportation (e.g., transit) of all the natural physiological process elements, whether presently identified or not, to facilitate tissue (e.g., including but not restricted to bone) regeneration to and from a source of multipotent mesenchymal cells and a wound and/or implant site. The structure is termed a conduit because transit can be in both directions and because many paths for physiological activities are provided within the conduit, including vascular systems, to allow continuous or sequential stages of repair. The conduit protects its contents from surroundings, which may include biological, chemical, and/or physical forces. The contents can include a multitude of physiological components that participate in converting genetically programmed responses to cellular and/or tissue responses at the wound sites. None of these features require external intervention after setting up the conduit.

As described herein, a conduit can include one or more segments formed at least in part from an osteoceramic material. For example, a conduit can include one or more segments and, depending upon the particular application, can also include other structures contributing to the transit (e.g., delivery) of the multipotent mesenchymal cells and/or products thereof, etc., and/or contributing to the support and/or appropriate tissue regeneration of the damaged tissue. One or more segments of the conduit can enable transit of multipotent mesenchymal responses (e.g., the cells and/or their products), along with other cells, cell products, and/or blood, from one or more sources to a targeted site and/or the vicinity thereof. The conduit can provide a sheltered environment for transit of the multipotent mesenchymal responses, etc., to the target. The conduit can transit the tissue building components to and from the target site such that a geometrical construction of the conduit can control regenerated tissue structure. For example, the geometrical construction of the conduit can control bone structure and microstructure to promote and guide bone formation, bone growth, and/or bone strength to produce normally functional bone and associated tissue at the targeted site.

In some examples, the conduit can carry a fluid (e.g., blood, lymph, plasma, etc.) that serves as a transport medium for active components of wound healing and/or tissue regeneration, which can increase the kinetic rates of the wound healing and/or tissue regeneration. The conduit can define a pathway and/or orientation of structures (e.g., vascular and/or endosteal systems) that become connected from sources to targets. The conduit can serve as a barrier (e.g., with impervious walls) to excessive fluid and/or cell leakage and/or callus formation. The conduit can provide strength to withstand external forces imposed by surroundings and/or functional stresses imposed by the bodily location in which it is utilized in order to protect the associated tissue.

The conduit described herein is fabricated from suitable material(s). Because multipotent mesenchymal cells are typically sequestered in protected areas of the skeleton (e.g., the diaphysis of long bones, the ileum, the sternum, etc.), conduit walls can be constructed of an artificial bone having suitable tissue response and physical properties. The osteoceramic material described herein is suitable. The principles herein are described in the context of orthopedic applications by way of example and not by way of limitation, as they can be applied to all types of tissue repair. That is, although bone is used to illustrate the use of the conduit, the principles apply to tissue repair in general wherever access to multipotent mesenchymal cells is beneficial and/or possible. For soft tissue purposes, the conduit also can be fabricated using natural tissue sources (e.g., vascular tubes, fallopian tubes, among others).

Provision of a conduit as disclosed herein provides for necessary cells of all types, provides a connected blood supply system to participate in wound healing, to control hematoma and callus formation, to provide for development of a new blood supply to transport the mesenchymal cell responses to the tissue growth areas adjacent to the implant, and to provide a mechanism for bone to attach to an implant. The present disclosure provides a method to allow the natural physiological processes of the patient to deliver the mesenchymal cells that form osteogenic cells to the areas of the tissue adjacent to an implant or trauma so that the cells can generate new tissue. The method is made possible during the surgical procedure by installing a conduit from the natural location of the mesenchymal cells to the areas adjacent to the site where tissue is needed for stabilization of the implant/tissue structure and to provide the strength necessary for said implant/tissue structure to support the loads necessary for normal function of that part of the body.

Using orthopedic repair as an example, the present disclosure also includes provision for a blood supply within the conduit and the areas adjacent to the implant that facilitate the normal physiology of wound healing and bone generation necessary for the load-bearing implant/bone structure to perform its function. This disclosure can extend the manufacture of mesenchymal stem cells into the conduit closer to the areas adjacent to the implant by providing the necessary conditions for that extension to occur. This disclosure also provides the geometry and composition of the implant structure to allow the natural physiological process of bone regeneration to operate by providing space to induce and/or allow the bone regeneration to occur, to control the geometry of the new bone, to provide a strong bond of bone to the implant, to allow for the physical stresses that might otherwise destroy the conduit as bone through which it passes receives the applied load, and, where appropriate, to provide a calcium phosphate environment within the conduit to the bone regeneration areas. The above accomplishments induce the bone to regenerate and/or to achieve stabilization in a much shorter time than would be possible without the conduit.

This disclosure provides for the conduit to be divided into segments to expedite the surgical procedure and for some segments to be within or on the surface of the implant to expedite the delivery of osteogenic cells to the areas of bone regeneration adjacent to or within the implant. The conduit method is applicable to any surgery where transport of tissue generating components is needed. This includes soft tissue and organ generation, as well as bone generation, and all are included within the scope of this disclosure. Bone generation is used as an example in the embodiments of the methods, apparatuses, and systems described herein, but other applications can utilize the same concepts. Two examples are provided herein for the application of the conduits to satisfy urgent orthopedic needs. A myriad of other soft and hard tissue applications are possible.

DETAILED DESCRIPTION OF THE DISCLOSURE

Reference will now be made in detail to particular embodiments of the present disclosure, which together with the following examples serve to sufficiently describe and explain the principles of the invention so as to enable one of ordinary skill in the art to make use of this disclosure.

The impetus for this endeavor was a request from the chief surgeon in the joint military program to defeat improvised explosive devices and to help amputees who have insufficient bone for prosthesis attachment. This caused the inventor to re-examine earlier research and patents to try to find a method of modifying a patient's orthopedic implant possibilities to facilitate attachment of prostheses. In reviewing the research for U.S. Pat. No. 6,312,467, McGee, issued Nov. 6, 2001, the inventor discovered the original notes made by radiologists who evaluated the osteoceramic bone bridge with the geometry having longitudinal grooves on the surface to guide tissue formation and cause encapsulation of the implant with load-bearing bone and having notches for tissue attachment at the ends. These notches were filled with trabecular bone and the implant was surrounding an exterior cortex that was contiguous with the original bone at each end. The new cortex encapsulated the entire implant, providing the stable result that was desired. The temporary support was removed after 13 months. When the dog died ten years later, the implant was still stable with only the tissue bonded to the bone for stabilization. In this study, the radiologist noted new dense bone only one month after the surgery in contact at each end of the implant. This is contrary to the conventional callus, fibrous support, and cartilage-spongy bone-remodeling to dense bone sequence in the state of the art for bone healing. It is also contrary to the time sequence thereof. Note that the soft tissue structure must have formed even more rapidly before mineralization occurred to provide radiographic density.

Rejecting the conventional understanding of bone healing and based on this new finding, the inventor re-examined the wound and bone generation prior art. Instead of the conventional sequence in healing and generating new bone based on sequential delivery of cells, formed elements of the blood, unknown signals triggering cytokines and growth factors, the inventor conceived that the necessary components are always available in the multipotent mesenchymal cells and blood, etc. Particular cells dominate at a particular time because the targets of the particular cells are abundant. It is like a chemical reaction where high concentrations of the reactants drive the reaction to move toward equilibrium by rapidly making products.

There are a number of histologically rich sources of multipotent mesenchymal cells, for example, at all ages (e.g., fetal, pediatric, adult) in bone marrow, adipose tissue, liver, and muscle tissue, in a developing tooth bud of the mandibular third molar, in amniotic fluid, in addition to the umbilical cords of newborns. Adequate blood supply and a vascular system to transport all the osteogenic components, for example, are necessary. A conduit as described herein can carry (e.g., transit) all of the necessary components. This conduit can connect the sources directly to the site where there is a need instead of relying on a large-scale systemic response. Also described herein are devices, the conduit itself and its parts, the structural features of the conduit, the geometry, the necessary instruments, and the associated implant features.

As expressed above there is a need for utilizing the multipotent mesenchymal cells of a patient to span a critical loss of bone and to cause bone to bond rapidly to an implant in such a way that the new bone and the implant, acting as a unit, can support the normal loads in the functions normally required for that portion of the skeleton in which the implant is introduced. Using concepts of this disclosure, the patient can be freed from trauma and morbidity of an autograft, the infections and immune problems of allografts and xenografts, and the deficiencies in the bone strength and structure inherent in the bone graft substitutes and bone void fillers provided by the tissue engineering practice described above.

Orthopedic implants previously used for hip and knee joint replacements do not have beneficial contact with bone marrow containing multipotent mesenchymal cells. All their components are inert and become walled off by a fibrous capsule, in a foreign body reaction. They must be mechanically anchored in place. Other orthopedic procedures also do not have access to mesenchymal cells. There is a need for a way to supply the benefits of a multipotent mesenchymal cell response, along with associated cells and products, to an implant site to enhance tissue regeneration. The implementation of the conduits described herein serves that purpose.

Each particular implant surgery and/or fracture repair is different. While inspired by an interest in artificial bone grafts, the methods, apparatuses, and systems described herein can also be used for severe fractures or for any surgery where there is a source of multipotent mesenchymal cells nearby and/or where a viable source of multipotent mesenchymal cells can be provided. Having located the source and the wound healing locations, a conduit can be placed between the nearest source of mesenchymal cells and the surgical site. In the case of bone, holes can be drilled to accommodate the conduit. The conduit can be appropriately inserted and can have functional structure (e.g., an enclosed, hollow, tubular conduit of any cross-sectional configuration, such as round, square, rectangular, oval, or irregular in order to suit the particular implantation site) having open ends to connect the mesenchymal source to the target site. This constitutes at least part of a conduit for blood and for mesenchymal cell responses, growth factors, etc.

In some examples, marrow or another histologically rich source of multipotent mesenchymal cells can be harvested from the source and smeared on the inside and/or outside of the conduit to provide a continuous conducting pathway for transit of mesenchymal and osteogenitor cells, etc., on the surface. Afterwards, the conduit will fill with blood and clots will form. The clots will be removed by scavenger cells, such as scavenging leukocytes (especially monocytes), macrophages, osteoclasts, and fibroclasts, etc. At nearly the same time, the vascular system will provide a pathway for messenger proteins, such as growth factors. Once the conduit is connected, stable and rapid regeneration of bone will occur and will continue until the bone is repaired.

For bone repair, the conduit must be strong enough to withstand the forces applied on it by its surroundings and the conduit should be compatible chemically with the interior contents of the body. Because of its strength and the calcium phosphate content of the conduit wall, the osteoceramic material specified herein has the necessary strength and compatible chemistry. The conduit includes the stable environment and blood supply induced by the mesenchymal cells and compatibility from the soluble calcium phosphate at the internal and/or external surface of the conduit. The conduit, in some examples, can pass through trabecular bone to reach the bone marrow. Local repair of the trabeculae will occur very quickly so those segments of the conduit must be strong enough to support the load the trabeculae will impose on the conduit as they encompass it to support the stresses in the interior region of the bone.

Because the contact area of an implant can be large, and because the conduit described above with two open ends only transits the active components (e.g., multipotent mesenchymal cell responses, multipotent differentiated cells, accessory cells, growth factors, etc.) to one location chosen near the target of the implant, the implant can have openings, holes, perforations, and/or channels to connect the transit (e.g., delivery) of multipotent mesenchymal cells, etc., to other locations at and/or proximal to the trauma site (e.g., such as to the periphery of the implant). These openings, holes, perforations, and/or channels then are a part of the conduit system. The same requirements for its physical strength and/or composition can apply to various segments of the conduit. The osteoceramic material described herein satisfies that need.

Ultimately, the openings, holes, perforations, and/or channels of the conduit will usually be filled with cortical or trabecular bone and will become a strong, stable part of the conduit-and-functional-bone assembly to support the conduit in its skeletal function. The position and shape of the openings, holes, perforations, and/or channels allows them to serve as guides to control whether trabecular or cortical bone is regenerated. Generally, cortical bone is induced to form on the exterior surfaces of the conduit to encapsulate it and to be continuous with the adjacent bone, and trabecular bone is formed within the conduit.

Methods are disclosed for delivering active osteogenic components, such as blood, blood vessels, mesenchymal cell responses, multipotent differentiated cells, accessory cells, cytokines and growth factors from an origin within the patient to the critical location necessary for soft and hard tissue repair. The methods are illustrated using examples of bone formation to support an orthopedic implant or to mend a bone defect and/or fracture by providing a conduit for that purpose. The components delivered by the conduit include those necessary for soft and hard tissue wound healing and soft and hard tissue generation and/or regeneration. Because osteogenic components participate in bone regeneration, devices are disclosed for design, construction, installation and application of the conduit. Examples are given for surgical application of conduit methodology. The conduit may include one or more segments and may include multiple origins. Some parts of the conduit may be within the implant geometry. The methods, apparatuses, and systems can activate and surgically repair by tissue generation and/or regeneration, and attachment processes that are faster than current methods or are not possible by current methodologies.

Figure 2:
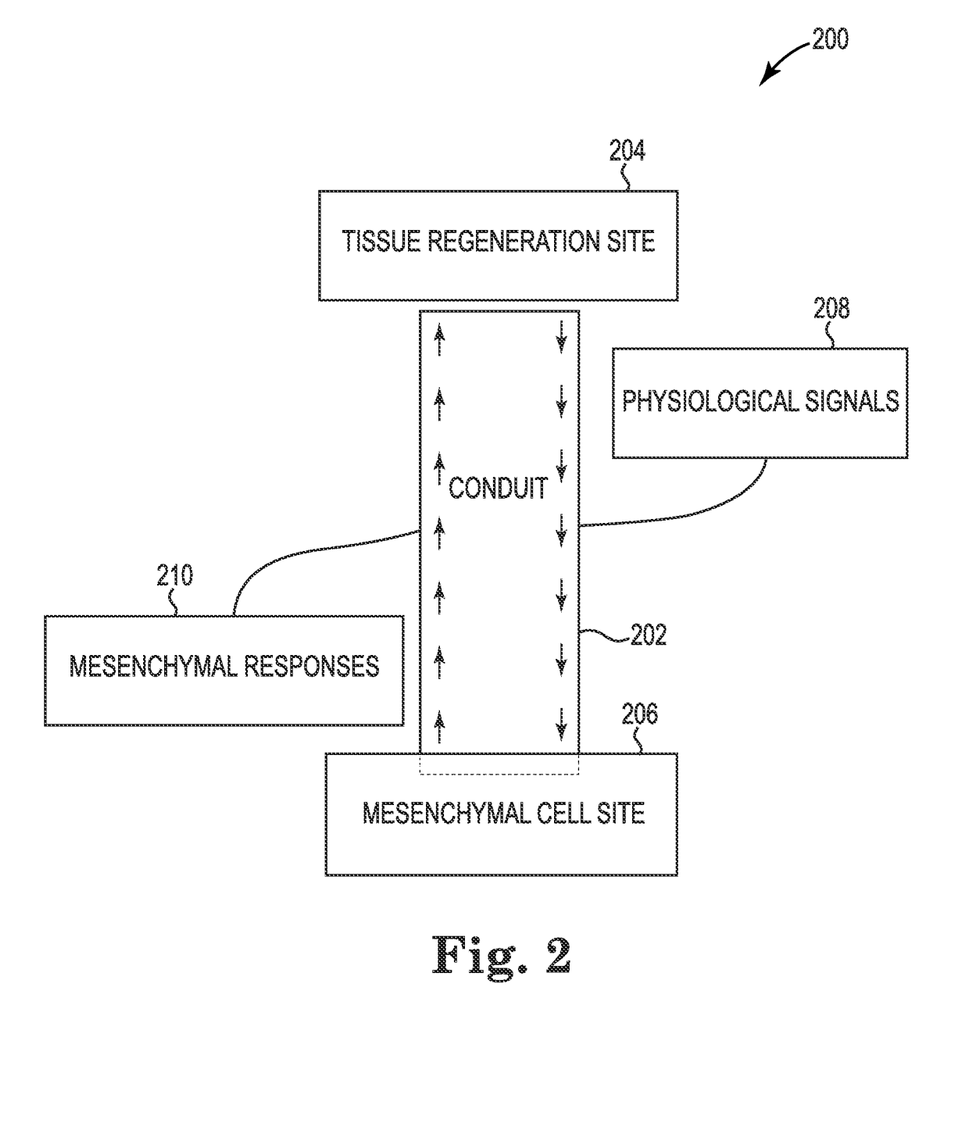
FIG. 2 is a block diagram illustrating an example of a conduit for enhancing tissue regeneration according to the present disclosure.

FIG. 2 is a block diagram illustrating an example of a conduit for enhancing tissue regeneration according to the present disclosure. Unless explicitly stated, the method examples described herein are not constrained to a particular order or sequence. Additionally, some of the described method examples, or elements thereof, can occur or be performed at the same, or substantially the same, point in time.

In the detailed description of the present disclosure, reference is made to the accompanying drawings that form a part hereof and in which is shown by way of illustration how examples of the disclosure may be practiced. These examples are described in sufficient detail to enable those of ordinary skill in the art to practice the examples of this disclosure and it is to be understood that other examples may be utilized and that process and/or structural changes may be made without departing from the scope of the present disclosure. Further, where appropriate, as used herein, "for example" and "by way of example" should be understood as abbreviations for "by way of example and not by way of limitation".

The figures herein follow a numbering convention in which the first digit or digits correspond to the drawing figure number and the remaining digits identify an element or component in the drawing. Similar elements or components between different figures may be identified by the use of similar digits. For example, 111 may reference element "11" in FIG. 1, and a similar element may be referenced as 211 in FIG. 2. Elements shown in the various figures herein may be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense.

The example of a conduit for enhancing tissue regeneration 200 illustrated in FIG. 2 shows the conduit 202 to be a single segment (e.g., with a top to bottom length) with a first end opening at the tissue regeneration site 204 (e.g., soft and/or hard tissue wounds and implant sites) extending to a second opening immersed in a multipotent mesenchymal cell site 206. Physiological signals 208 from the tissue regeneration site can migrate directly through the conduit 202 to the multipotent mesenchymal cell site 206, where they can stimulate the mesenchymal cells to differentiate into tissue generating responses 210 (e.g. cells, cytokines, growth factor, etc.) that can migrate directly through the conduit 202 to perform tissue generating functions at the tissue regeneration site 204.

Additional conduit segments (lengths) may be added in series if needed. For example, if other sources of mesenchymal cells are also required, the conduit can pass through different types of tissues (e.g., from hard to soft or vice versa) or, if it is necessary, to accommodate anatomical features where different cross sectional geometries are needed. The walls of the conduit 202 or various segments thereof can be rigid or flexible depending on anatomical and functional features.

The conduit provides a direct connection between the tissue regeneration site 204 and the multipotent mesenchymal cell site 206. The physiological signals 208 from the tissue regeneration site 204 are not completely understood but are known to exist. As healing proceeds, the physiological signals 208 can change so the healing process is dynamic in time. The mesenchymal cell differentiation products are also not completely understood and can vary in time but are known to exist. Part of the difficulty in understanding the healing processes is that the processes are very complex and the signals and responses are delivered systemically where great dilution can occur and some signals or responses may not be able to pass through anatomical barriers. Experimental evidence cited herein shows that the direct connection through the conduit is faster and that the bone produced provides a direct connection of load-bearing bone instead of producing the usual huge chondroital callus that must be removed by a remodeling process requiring months or years to complete.

As described in the present disclosure, tissue regeneration can include a site 204 where wound healing and tissue regeneration are needed that releases physiological signals 208 into the first open end of a conduit 202 to be transmitted through the conduit directly to the second opening of the conduit 202 at the mesenchymal cell site 206, stimulating the mesenchymal cells to differentiate into tissue generating responses 210 to be transmitted directly to the first opening of conduit to accelerate healing and generating at the site 204.

As described in the present disclosure, a method of enhancing tissue regeneration by providing an interactive connection between a tissue regeneration site 204 and a histologically rich multipotent mesenchymal cell source 206. The method can include originating at the tissue regeneration site 204 a first open end of a conduit structure 202, the conduit structure composed of a number of segments, promoting physiological signals 208 to transit from the first open end to the source of the histologically rich source of multipotent mesenchymal cells 206 at a second open end of the conduit structure 202, promoting at least some of the multipotent mesenchymal cells to produce tissue regeneration response products 210, and promoting at least some of the tissue regeneration response products 210 to transit to the first open end to enhance the tissue regeneration.

Examples 1-2 below are illustrative of the principles of the present disclosure for conduit transit (e.g., delivery) of the multipotent mesenchymal and/or osteogenic cells, and products thereof, etc., for guided soft tissue and/or bone regeneration, as described herein. These examples are intended in an illustrative sense and are not to be construed in a limiting sense because various other embodiments can readily be conceived in view of the teachings provided herein.

Example 1

Perthes Disease Repair

Perthes disease can occur when the femoral artery to the ball of the hip joint is destroyed or blocked. Perthes disease occurs most frequently in children and young adults, especially to highly athletic young men who are using non-steroidal anti-inflammatory medication. Alcoholic consumption may contribute. When the blood supply to the ball is interrupted, necrosis of the bone in the ball can set in. This can weaken the ball and fracturing can occur. This tends to flatten the ball. Pain is usually present and movement becomes more difficult. The contact area of the acetabular cup loses its spherical shape as it conforms to the misshapen ball and the patient has serious impairment of the function of the joint. It is possible for the ball to recover sufficient for nearly normal function in patients that are young enough to be still growing when spontaneous recovery and remodeling is complete. If the patient reaches puberty before the remodeling is complete, dysfunction will remain. Increasing the rate of recovery and/or lengthening the deterioration progress before fracturing or disintegration of the ball can occur would greatly enhance recovery. A new blood supply and availability of an osteogenic system (e.g., derived from multipotent mesenchymal cells, etc.) to enhance rebuilding of the ball are urgently needed for Perthes disease patients. A conduit for rapid regeneration and/or for restoration of the necessary blood supply, as described herein, satisfies that need.

Figure 3:
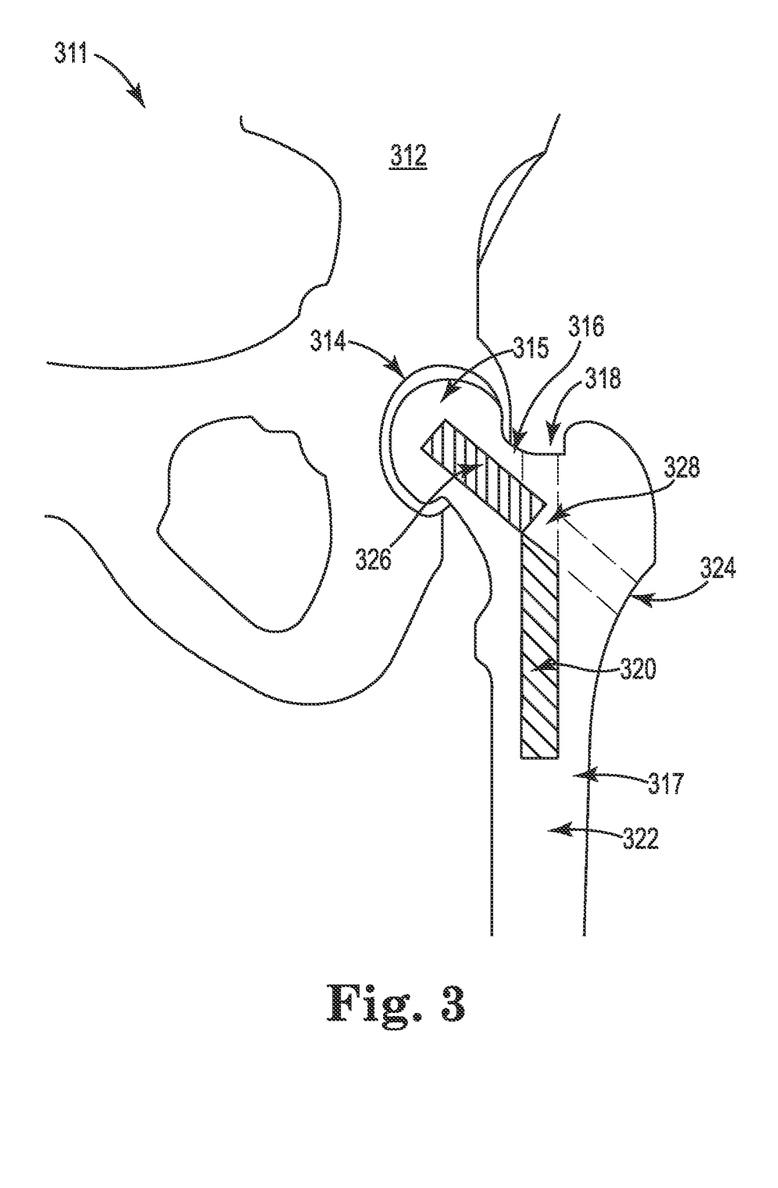
FIG. 3 illustrates an example of a conduit for enhancing tissue regeneration implemented for a condition according to the present disclosure.

FIG. 3 illustrates an example of a conduit for enhancing tissue regeneration implemented for a condition according to the present disclosure. The example of enhancing tissue regeneration with a conduit 311 illustrated in FIG. 3 represents treatment of Perthes disease associated with a ball 315 of a femur 317 of a human patient. A hip socket 314 (e.g., acetabulum) is formed in the pelvic girdle 312 from three intersecting bones (e.g., the ilium, the ishium, and the pubis). The axis of the ball 315 and the neck 316 makes an angle of about 45° with the shaft of the femur 317 for insertion into the acetabular socket 314. The midshaft region of the femur 317 has a femoral marrow cavity 322 that contains marrow rich in multipotent mesenchymal cells. The distal region of the neck 316 is rich in hematopoietic mesenchymal cells that supply blood regeneration products. Access to the multipotent mesenchymal cells 322 can be made by drilling a first access 318 (e.g., drill hole, tunnel, etc.) from the notch of the greater trochanter axially through trabecular bone into the femoral marrow cavity 322. A second access 324 (e.g., drill hole, tunnel, etc) can be drilled through the lateral aspect of the femur 317 into the neck 316 on its central axis to reach the ball 315 of the femur 317. Inserting a first osteoceramic conduit segment 320 into the marrow cavity 322 through the first access 318 from its distal terminus in the marrow 322 to the proximal intersection 328 with the second access 324 provides the first segment of the mesenchymal cell conduit. Inserting a second osteoceramic conduit segment 326 through the second access 324 to reach from the intersection 328 with the first osteoceramic conduit segment 320 to an intended position in the ball 315 provides the second hematopoietic mesenchymal cell segment of the conduit. Segments 320 and 326 constitute two segments of the conduit.

Example 1 has features that pertain to the flexibility a surgeon has in utilizing the conduit method. If the Perthes disease is in its earliest phase, where blood supply is critical, the surgeon has the option of using only a single segment of the conduit 326 shown in FIG. 3. Only a single access hole 324 would then be drilled. This will give the ball 315 access to the hematopoietic stem cells in the epiphysis to improve the blood supply to the ball 315.

If the Perthes disease at the time of surgery is in a later stage, where the rate of bone regeneration is critical, the opening 328 at the intersection of segments 320 and 326 could be closed by using a segment 326 that fits tightly to segment 320. This requires an extension of 326 with an opening at the open end of segment 320. This constitutes a system for conduit use.

For this example, the cross section of the segments 320 and 326 can be circular to fit closely in their respective holes. The segments have the shape of hollow tubes with rigid walls. The composition, geometry (e.g., such as wall thickness and/or length), strength, impermeability, and outside diameter are selected to be suitable to perform its functions. The surgeon can have a supply of osteoceramic conduit segments from which to choose.

In some examples, bone marrow can be applied (e.g., transferred from the bone marrow cavity 322 by smearing) to the inside and/or outside of the first and/or the second osteoceramic segment 320, 326 before insertion of the first access 318 and/or the second access 324 to promote and/or enhance the transit (e.g., proliferation and/or migration) function. At least a partial opening (e.g., open space) at the intersection 328 of the first and/or the second osteoceramic segment 320, 326 can allow the rich blood supply of trabecular bone at that location to fill the osteoceramic cannular structures with blood, which can clot and then remodel to become axial blood supplies. The hollow core of the second osteoceramic segment 326 extends to the ball 315, which enables the multipotent mesenchymal cell response products and contents of the axial blood supply to transit to the ball 315 to stop necrosis and induce regeneration of the ball 315.

The second osteoceramic conduit segment 326 near the center of the ball 315 can have openings, holes, perforations, and/or channels through a wall thereof to distribute the blood supply and osteogenic elements therethrough to the adjacent and/or surrounding (e.g., proximal) tissue. When the clot becomes vasculated, the conduit can then serve to transit blood, growth factors, multipotent mesenchymal cells, osteogenic cells, osteoclasts and osteoblasts, fibroclasts, fibroblasts, and chondroclasts and chondroblasts, etc. The patient's own multipotent mesenchymal cells and the natural physiological process of wound healing, scavenging of dead tissue, and/or regeneration of bone are able to operate freely to rebuild the normal bone structure of the ball 315. If completed early enough, this can happen rapidly and prevent the flattening of the ball and the distortion of the acetabular socket 314. When flattening has already begun, recovery can be enhanced by the rapid repair and regeneration of new bone.

As described herein, the accesses 318, 324 (e.g., drill holes, tunnels, etc.) can be drilled to accommodate segments of the osteoceramic segments 320, 326 that contribute to forming the conduit. The vertical access 318 is drilled to extend to (e.g., into) the marrow source 322 at the diaphysis of the femur 317. The access 324 drilled into the neck 316 and the ball 315 reaches the destination in the ball 315.

A first conduit segment 320 can, for example, be placed first to provide access to the multipotent mesenchymal cells in the marrow 322 in the diaphysis of the femur 317. In some examples, the upper extent of the vertical conduit segment (e.g., proximal to the ball 315) can be at or just below the intersection 328 of the two accesses 318, 324, allowing for a second conduit segment 326 to be placed axially in access 324 to reach the neck 316 and the ball 315 to deliver the multipotent mesenchymal cells, blood, and osteogenic components, etc., to the ball 315. A rich blood supply and hematopoietic stem cells exist in the trabecular bone at the intersection 328 of the conduit segments (e.g., 320, 326) to supply additional blood through the partial opening at the intersection 328 to the second conduit segment (e.g., osteoceramic cannular structure 326) for the neck 316 and/or the ball 315.

Marrow in the cavity 322 in the diaphysis of the femur 317 is protected from physical stresses because it is surrounded by dense cortical bone. The blood supply to that area is provided through foramina (e.g., openings, not shown) that deliver external blood to the interior primarily to supply the functional interior lining of the cortex, the endostium. The first segment of the conduit 320 within the trabecular portion of the bone near the epiphysis can be strong enough to withstand the external forces that are delivered to it as the trabeculae reform during wound healing (e.g., by being formed to include osteoceramic material, as described herein). As such, the internal spaces of the bone and the conduit can be shielded from physical stress. Therefore, first segment of the conduit 320 can, in effect, become a new cortex that allows marrow to enter into that segment of the conduit, enabling the multipotent mesenchymal cells and/or products thereof to proliferate and/or migrate therein and transit closer to the intended destination (e.g., target) of the conduit.

Accordingly, as described in the present disclosure and consistent with the embodiment illustrated in FIG. 3, an apparatus to enhance bone regeneration can, in various embodiments, include a first number of conduit segments formed from a material comprising calcium phosphate, at least one of the conduit segments having a first open end at a bone healing site and a second open end at a source of multipotent mesenchymal cells. Physiological signals from the bone healing site can transit the conduit to stimulate the mesenchymal cells to differentiate into osteogenic responses that transit the conduit to the bone healing site to regenerate new bone. The conduit segments can, as described in the present disclosure and consistent with the embodiment illustrated in FIG. 3, form an extravascular or transvascular conduit for the multipotent mesenchymal cells and/or products thereof to enhance bone regeneration.

In some examples, at least one of the first number of conduit segments and at least one of the second number of conduit segments can form a single continuous conduit segment from the first open end proximal to the site of damaged bone to the second open end at the intramedullary bone cavity. Alternatively or in addition, in some examples, at least one of the first number of conduit segments and at least one of the second number of conduit segments can form longitudinal segments of the conduit having at least a partial opening between the segments (e.g., as illustrated in FIG. 3) for ingress and transit of additional functional cells, cytokines, growth factors, blood, and blood vessels, etc., to enhance the bone regeneration. In various examples, at least a portion of an inner surface of at least one segment can comprise calcium phosphate having a controlled rate of solubility in biological fluids to promote multipotent mesenchymal cell response transit therethrough and/or proliferation therein.

For mesenchymal cells in bone, the interior surface of a conduit segment can have a component comprising calcium phosphate to produce a chemical environment within the conduit. The calcium phosphate can be selected from the group including tricalcium phosphate, hydroxyapatite, oxyapatite, and/or fluoroapatite. The conduit can also be strong enough to withstand the physical forces imposed on the conduit. These requirements can be satisfied with a composite with interconnected phases of calcium phosphate and magnesium aluminate spinel. In various examples, an inert material (e.g., magnesium aluminate spinels) can be compatible with the calcium phosphate material in physical properties and chemistry during processing. The structure is similar to that of a sponge, with the skeleton composed of the spinel and the holes filled with calcium phosphate. This composition can also be used as an orthopedic implant and it can have geometric features as a segment of the conduit.

Details of forming osteoceramic components, including the microstructure, properties, and geometry thereof, are provided in U.S. Pat. No. 3,787,900, McGee, issued Jan. 29, 1974, and in U.S. Pat. No. 6,312,467, McGee, issued Nov. 6, 2001, which are incorporated by reference into this application. The McGee osteoceramic is a ceramic/ceramic composite containing various calcium phosphate materials, as presented herein, and spinel materials (e.g., magnesium aluminate, etc.) as an inert material (e.g., in a 50/50 volume percent ratio). The calcium phosphate material is used to control the tissue response and to confer biocompatibility. The spinel material is used to provide structural strength (e.g., to withstand torsional, tensile, compressive, and/or bending loads).

Example 2

Tibia Tuberosity Advancement

Figure 4:
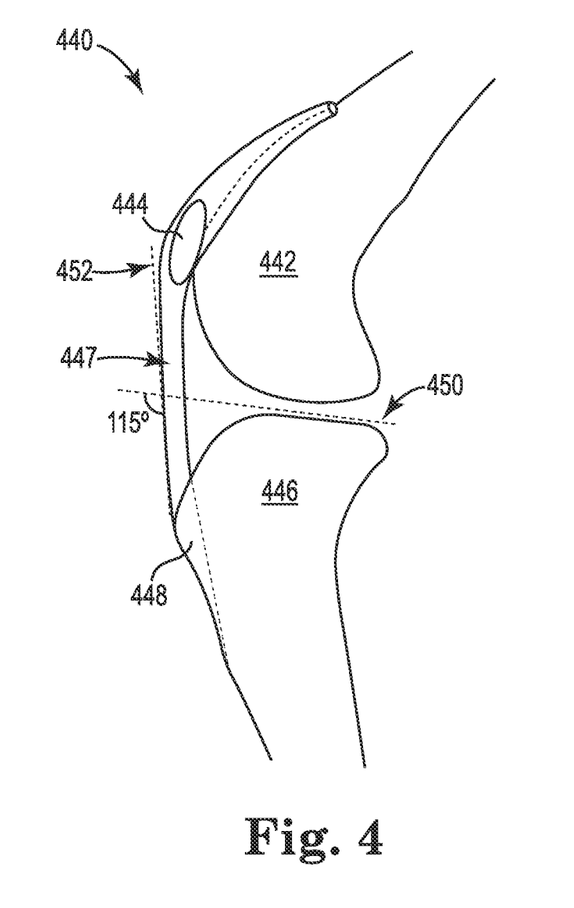
FIG. 4 illustrates an example of another condition for which enhanced tissue regeneration can be implemented consistent with the present disclosure.
Figure 5:
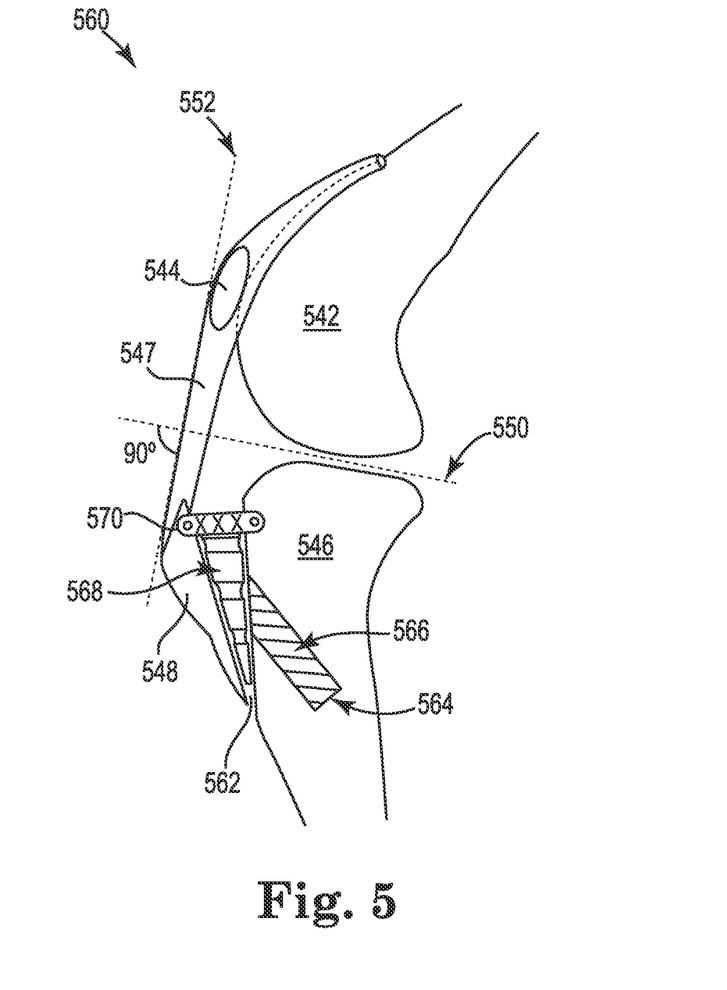
FIG. 5 illustrates an example of a system for enhancing tissue regeneration in which a first conduit segment connects with a mesenchymal cell source and features of an implant constitute a second conduit segment according to the present disclosure.

FIG. 4 illustrates an example of another condition for which enhanced tissue regeneration can be implemented consistent with the present disclosure. When a canine, for example, suffers an injury that weakens, tears, or breaks an anterior cruciate ligament (ACL), the knee joint can become unstable with the tibia sliding too far forward below the femur. This is a serious injury in all mammals. The example of ACL damage illustrated in FIGS. 4 and 5 represents damage to one knee of a canine patient by way of example and not by way of limitation. That is, the aspects of utilizing conduits for enhancing tissue regeneration described herein are not limited to treatment of knee joints and/or canines, and multiple injured soft tissues and/or bones could be treated simultaneously or sequentially if needed (e.g., in contrast to the applications shown in FIGS. 3-5 in which treatment of one joint is illustrated).

FIG. 4 illustrates a lateral picture of a normal canine knee 440 seen from a medial view, showing the bones and the anterior patella ligaments, but not the cartilage and the ligament band that attaches to the patella, nor other soft tissue features. In FIG. 4, the normal knee 440 features include the distal femur 442, the patella 444, the tibia 446, and the region of the tibia 446 to which the patella ligament 447 is attached, that is, an insertion point on the tibia tuberosity 448. Also shown is the angular relationship between the plane of the tibia plateau 450 and the plane of the patella ligament 452. The 115° angle between the tibia plateau 450 and the plane of the patella ligament 452 is an angle often found in dogs, although higher and lower angles can occur.

Accordingly, in various examples, a system to enhance tissue regeneration can include a number of segments of a conduit having a first open end at a tissue regeneration site to promote physiological signals to transit to a second open end configured for penetration into a histologically rich multipotent mesenchymal cell source. The physiological signals can promote differentiation of multipotent mesenchymal cells into tissue regeneration response products that transit the conduit to the tissue regeneration site to enhance the tissue regeneration. In some examples, a bioactive, biocompatible implant can be utilized to at least partially fill a void of partitioned bone. In various configurations, the bioactive, biocompatible implant can have openings that contribute to functionality as a conduit segment.

FIG. 5 illustrates an example of a system 560 for enhancing tissue regeneration in which a first conduit segment connects with a mesenchymal cell source and features of an implant constitute a second conduit segment according to the present disclosure. A repair, for example, that can make the knee joint more stable and/or can reduce risk of arthritis is Tibia Tuberosity Advancement (TTA). When the ACL is weakened, missing, torn, or broken, a change of the angle to about 90° of the plane of the tibia plateau 550 and the plane of the patella ligament 552, achieved by moving the tibia tuberosity ligament insertion point 548 forward, can provide a restoring force that at least partially compensates for the weakened, missing, torn, or broken ACL, so that the tibia 546 and/or the femur 542 do not slide forward. This is done by severing 562 the tibia tuberosity 548 and shifting it to an anterior position as shown in FIG. 5.

To fix the tibia tuberosity 548 in an intended position, a cage and/or bracket 570 (e.g., formed from a strong and biologically enduring material, such as metal) can be inserted between the patella ligament 547 attachment end of the tibia tuberosity 548 and a cut surface of the remaining tibia 546 at the end by the tibia plateau 550, and fixed with, for example, one screw in the tuberosity and one in the tibia. This establishes a distance of the forward advancement of the tuberosity at the insertion point. Note that this can result in an open space (e.g., in the shape of an irregular triangular prism) between the cut surfaces of the tibia 546 and the tibia tuberosity 548. Various numbers and/or configurations of cages and/or brackets 570 can be placed under the patella end of the tibia tuberosity 548 and fixed in place, for example, with extensions on the medial side screwed to the tibia tuberosity 548 and/or to the underlying tibia 546. Cages and/or brackets and/or ancillary fixation (not shown) to the underlying tibia 546 proximal to an end of the tibia tuberosity 548 distal from the patella end can support the tensile force of the patella tendon and/or prevent the tibia tuberosity 548 from moving when that force is applied.

Such corrective surgery may help stabilize the knee, but recovery time can be greatly prolonged because a significantly large open space (e.g., in the shape of an irregular triangular prism) remains to be replaced by bone. Although an autogenous bone graft can be harvested from elsewhere in the skeleton, the recovery time can take many weeks, regardless of whether "bone void fillers" are utilized. Therefore, there is a need for a better method to fill the gap between the cut surface of the tibia tuberosity 548 and the cut surface of the tibia 546.

As described in the present disclosure, the open space can be filled with a bioactive implant with enduring strength formed from osteoceramic material, for example, as formulated (e.g., by molding, cutting, stereolithography, etc.) in the shape of a wedge 568. Such a wedge 568, having planar surfaces to fit the cut surfaces and/or being contoured on lateral and/or medial aspects to fit the open space geometry, can provide immediate support to the tibia tuberosity 548 and can reduce the volume of new bone required to fill the open space and the time required to attach the wedge 568 to both cut surfaces of the bone is greatly reduced.

To provide for multipotent mesenchymal cell response migration to the bone regeneration sites and/or to provide a blood supply to the tibia tuberosity 548 and/or the regenerating bone, grooves can be formed in the wedge 568 (e.g., as are shown in FIG. 5, although not limited to such a configuration). Such grooves can serve other functions, such as to guide the healing bone to providing an intended support structure and/or to induce encapsulation of the wedge 568 in cortical bone, among other functions. In various examples, the wedge 568 can be constructed from more than one component to give more flexibility in surgical applications. A surgeon can thus select from an array of wedge components to fill the open (e.g., wedge-shaped) space. A wedge formed from osteoceramic material can be made as a fired ceramic, a moldable ceramic, and/or a cemented ceramic.

As described with regard to Example 1 and FIG. 3, tissue regeneration can be greatly expedited through use of conduits for transit of multipotent mesenchymal cell responses, differentiation products, etc., as described herein. To provide a conduit to enable transit of the mesenchymal cells, products thereof, differentiated osteogenic cells, and other components contributing to new bone formation and wound healing, before fixing the tibia tuberosity 548 to the tibia 546 with the one or more cages and/or brackets 570, an access 564 (e.g., drill hole, tunnel, etc.) for the conduit can be constructed by moving the tibia tuberosity 548 aside and drilling into the trabecular bone of the tibia 546, for example, starting near the center of the cut surface at an angle to reach a marrow cavity located near mid-shaft of the tibia 546.

A length of the access 564 can be measured. An osteoceramic conduit segment 566 of a suitable length can be inserted into the access 564 to reach the marrow in the marrow cavity. The osteoceramic segment 566 can be formed with a chamfer on one end proximal to the tibia tuberosity 548 to make that end parallel with the cut surface of the tibia 546. In some examples, a device (e.g., constructed similar to a pipe cleaner brush) can be inserted sufficiently deep into the marrow and subsequently withdrawn (e.g., with rotation) to distribute marrow on an inner surface of the osteoceramic segment 566.

The osteoceramic conduit segment 566 becomes the first segment of the conduit described with regard to FIG. 5. The same device or a different device can be used to smear marrow in and/or on surfaces, holes, and/or grooves of the wedge 568 and/or in between the array of wedge components, such that a marrow trail is complete to the new bone regeneration areas (e.g., targets). Other examples of marrow transfer devices can include inflatable balloons and/or collapsible disks, among others. The osteoceramic wedge 568 becomes the second segment of the conduit described with regard to FIG. 5 when the wedge is in place and stabilized, thus completing the conduit for multipotent mesenchymal cell responses, osteogenic cells, and other components contributing to new bone formation and wound healing.

Accordingly, as described in the present disclosure and consistent with the embodiment illustrated in FIG. 5, a system to enhance bone regeneration can, in various embodiments, include a number of segments having a first open end proximal to a bone healing site to transmit physiological signals from the implant site to a second open configured for penetration of an intramedullary bone cavity to contact multipotent mesenchymal cells. The number of segments can have a second open end configured for egress of the multipotent mesenchymal cell response products through the conduit to the first open end and the implants site, causing the regeneration of partitioned bone. The system can have a bioactive, biocompatible implant to at least partially fill a void of the partitioned bone. Accordingly, the number of segments and the bioactive, biocompatible implant can form a conduit for the multipotent mesenchymal cell response products, osteogenic response products, etc., to enhance the bone regeneration to fill a remaining void of the partitioned bone with new bone.

In various examples, the number of segments (e.g., cannular structures) can be formed from an osteoceramic material, as described herein. The first open end of the number of segments for egress of the multipotent mesenchymal cell response products, etc., can be configured to substantially match a shape and angle of a surface of the partitioned bone proximal to the implant. In some examples, the conduit can be formed from a plurality of segments consistent with the description provided for Example 1 and FIG. 3.

In various examples, the implant can be formed from an osteoceramic material, as described herein. In some examples, the implant can be configured as a wedge to separate a portion of the partitioned bone having an attachment site for a ligament or a tendon from an underlying portion of the portioned bone. In various embodiments, the implant can be formed from a plurality of segments that are selectable from various shapes and sizes to more effectively fill the void of the partitioned bone. For example, the wedge can be formed from an array of wedge components. The implant can be configured, in various embodiments, to have surfaces that substantially match surfaces of the partitioned bone to reduce the void of the partitioned bone. The implant can be configured, in various embodiments, to have a shape and a number of perforations, channels, and/or grooves to guide bone regeneration to fill the void of the partitioned bone with new bone in order to enable the new bone to serve an appropriate bodily function.

In various examples, the system can include a number of cages and/or brackets between opposing surfaces of the partitioned bone configured to maintain an intended separation distance of the partitioned bone. The number of cages and/or brackets can, in various embodiments, be configured to reduce relative movement of portions of the partitioned bone.

The two examples described herein and illustrated in FIGS. 3 and 5 illustrate the principles of the methods and examples of structures utilized for construction. Variations and/or combinations of these methods and structures can be used for various fractures, implants, and surgical situations. All such applications are included in the scope of the present disclosure. The principles of the methods and the examples of structures described herein can be applied to soft tissue applications as well. The structure and properties of the conduit may be different but the functions will be basically the same. For example, a cardiac infarction may be treated using a flexible, tissue-compatible conduit from the sternum, where multipotent mesenchymal cells are available, to transit the multipotent mesenchymal cell response products thereof to the heart muscle target area of need.

Accordingly, consistent with enhancing tissue regeneration in hard and soft tissue, a method consistent with the present disclosure can include originating at a site where tissue generation is needed a first open end of a conduit, composed of one or more segments, stimulating physiological signals from said tissue generation site to migrate directly to a second open end inserted into the site of an histologically rich source of multipotent mesenchymal cells that respond to said signals to differentiate into tissue generating products that migrate directly through said conduit to said tissue regeneration site to stimulate the needed tissue regeneration. The conduit can be formed at least partially from an osteoceramic composite material.

In some examples, the first open end of a single segment can originate at the tissue regeneration site and can terminate at the second open end of the single segment proximal to the histologically rich source of multipotent mesenchymal cells (e.g., as described with regard to FIG. 5 and illustrated therein). In some examples, the first open end of a first conduit segment can originate at the tissue regeneration site and can terminate at the second open end of a second conduit segment proximal to the histologically rich source of multipotent mesenchymal cells (e.g., as described with regard to FIG. 3 and illustrated therein). In various embodiments, at least a partial opening can be formed between a second open end of the first segment and an adjacent first open end of the second segment for ingress and transit of additional functional cells, cytokines, growth factors, blood, and blood vessels to further enhance the tissue regeneration (e.g., as described with regard to FIG. 3 and illustrated therein).

In some examples, promoting the multipotent mesenchymal cells and/or products thereof to transit from the source can include coating at least a portion of an inner surface and/or an outer surface of at least one conduit segment with cells from the source of the multipotent mesenchymal cells to promote mesenchymal cell transit therethrough and/or proliferation therein. Alternatively or in addition, promoting the multipotent mesenchymal cells and/or products thereof to transit from the source can include coating at least a portion of an inner surface and/or an outer surface of at least one cannular structure with calcium phosphate having a controlled rate of solubility in biological fluids to promote mesenchymal cell transit therethrough and/or proliferation therein. In some examples, the coating can be inherent in the calcium phosphate composition of at least a portion of an osteoceramic conduit segment.

In various examples, terminating proximal to the target can include terminating proximal to a damaged bone structure and/or soft tissue to be regenerated. For example, the second open end of the segment can originate at the mesenchymal cell source to promote transit through the conduit of osteogenic cells to a number of sites proximal to the damaged bone structure. In various embodiments, a number of perforations or channels can be formed in a wall of the conduit proximal to the tissue regeneration first open end of the conduit segment at the tissue regeneration site to control a rate and/or location of the bone regeneration. As described herein, in some examples, at least a segment of the conduit can function as an orthopedic implant, where the source of the multipotent mesenchymal cells is in a bone structure adjacent to the damaged bone structure.

For example, the first conduit segment can be implanted as at least part of the conduit for the multipotent mesenchymal cells as utilized for enhancing tissue regeneration in treatment of Perthes disease of the hip (e.g., as described in Example 1 and with regard to FIG. 3 and as illustrated therein). For example, the first segment can be implanted as at least part of the conduit for the multipotent mesenchymal cells as utilized for enhancing tissue regeneration in Perthes disease repair and tibial tuberosity advancement (e.g., as described in Example 2 and with regard to FIG. 5 and as illustrated therein).

Accordingly, an apparatus to enhance bone regeneration, as described herein, can include a first number of segments formed from a material comprising calcium phosphate, at least one of the segments having a first open end configured for ingress of physiological signals proximal to a tissue regeneration site that promote multipotent mesenchymal cell differentiation and egress of mesenchymal cell differentiation products, and a second number of segments formed from a material comprising calcium phosphate, at least one of the segments having a second open end configured to penetrate a source of multipotent mesenchymal cells and configured for egress of the physiological signals and ingress of the mesenchymal cell differentiation products. In various examples, the segments can form an extravascular or transvascular conduit to enhance the bone regeneration.

Consistent with the present disclosure, tissue regeneration in bone and/or soft tissue can be enabled and/or supported by positioning a plurality of segments within a flexible external tube that is biocompatible to form at least part of a conduit. The flexibility of the tube can be envisioned as being similar to the flexibility of beads on a string, except that, in this instance, instead of the flexible string going through the inside of the beads, the flexible tube goes outside the plurality of segments and leaves the inside pathway of the plurality of segments open for transit of the multipotent mesenchymal cells, etc. To maintain the open pathway and/or provide strength, the plurality of segments can have an open end of a first segment formed in a convex configuration to articulate on an open end of an adjacent second segment formed in a concave configuration. In some examples, compatibility with surrounding tissue can be achieved by utilizing a flexible fabric and/or stent for the tube (e.g., made from an artificial, man-made material that, nonetheless, does not provoke a foreign body response and/or rejection). In some examples, compatibility with surrounding tissue can be achieved by utilizing a natural tube (e.g., a vein harvested from the patient).

Accordingly, a plurality of conduit segments can be supported with a flexible biocompatible external tube, in various embodiments, to form a flexible conduit. In some examples, at least a portion of the flexible biocompatible external tube can be formed from an artificial material. Alternatively or in addition, at least a portion of the flexible biocompatible external tube can be formed from a natural material.

It is to be understood that the descriptions presented herein have been made in an illustrative manner and not a restrictive manner. Although specific examples for apparatuses, systems, and methods have been illustrated and described herein, other equivalent component arrangements can be substituted for the specific examples presented herein without departing from the spirit and scope of the present disclosure.

APPENDIX

References

Janikowski, T., and McGee, T. D., Tooth roots for permanent implantation. Proc. Iowa Acad. Sci. 76, 1969, p. 113.
Park, J., and Lakes, R. S., *Biomaterials*, Springer, Vol. 3, 3rd ed., 2007.
Dorozhkin, S. V., *Bioceramics of Calcium Orthophosphate*, J. Biomaterials, 2009, p. 6.
Bone Graft Substitutes, Laurencin, C. T., Ed., (2003) written by a committee from ASTM International in conjunction with THE AMERICAN ACADEMY OF ORTHOPEDIC SURGEONS.

US Patent Documents

U.S. Pat. No. 3,787,900, McGee, issued Jan. 29, 1974
U.S. Pat. No. 6,312,467, McGee, issued Nov. 6, 2001
U.S. Pat. No. 6,364,909, McGee, issued Apr. 2, 2002
U.S. Pat. No. 6,719,793, McGee, issued Apr. 13, 2004

What is claimed:

1. A method of enhancing tissue regeneration by providing an interactive connection between a tissue regeneration site and a histologically rich multipotent mesenchymal cell source, comprising:
originating at the tissue regeneration site a first open end of a conduit structure;
promoting physiological signals to transit from the first open end to the source of the histologically rich source of multipotent mesenchymal cells at a second open end of the conduit structure;
promoting at least some of the multipotent mesenchymal cells to produce tissue regeneration response products; and
promoting at least some of the tissue regeneration response products to transit to the first open end to enhance the tissue regeneration;
wherein the concentration of multipotent mesenchymal cells at the tissue regeneration site is lower than the concentration of multipotent mesenchymal cells at the histologically rich multipotent mesenchymal cell source.

2. The method of claim 1, wherein the conduit structure is composed of a number of segments and the method further comprises forming the number of segments at least partially from an osteoceramic material.

3. The method of claim 2, comprising originating the first open end of a single conduit segment at the tissue regeneration site and terminating the second open end at the histologically rich source of multipotent mesenchymal cells.

4. The method of claim 2, comprising originating the first open end of a first conduit segment at the tissue regeneration site and terminating the second open end of a second segment at the histologically rich source of multipotent mesenchymal cells.

5. The method of claim 4, comprising forming at least a partial opening between a second open end of the first conduit segment and a first open end of the second adjacent conduit segment for ingress and transit of additional functional cells, cytokines, growth factors, blood, and blood vessels to further enhance the tissue regeneration.

6. The method of claim 1, comprising promoting the multipotent mesenchymal cells and/or products thereof to transit from the source by coating at least a portion of an inner surface and/or an outer surface of the conduit structure with cells from the source of the multipotent mesenchymal cells.

7. The method of claim 1, comprising promoting the multipotent mesenchymal cells and/or products thereof to transit to an open end of the conduit structure proximal to the tissue regeneration site by providing at least a portion of an inner surface and/or an outer surface of the conduit structure with calcium phosphate having a controlled rate of solubility in biological fluids.

8. The method of claim 1, comprising originating the first open end proximal to a damaged bone structure to be regenerated.

9. The method of claim 8, comprising structuring the first open end of the conduit structure at the tissue regeneration site to have a number of sites proximal to the damaged bone structure for egress of the tissue regeneration response products.

10. The method of claim 9, comprising forming a number of perforations or channels in a wall of the conduit structure to control a rate or a location for the egress of the tissue regeneration response products adjacent to the damaged bone structure.

11. The method of claim 8, comprising the conduit structure functioning as an orthopedic implant, wherein the source of the multipotent mesenchymal cells is in a bone structure adjacent to the damaged bone structure.

12. The method of claim 2, comprising supporting a plurality of conduit segments with a flexible biocompatible external tube to form a flexible conduit.

13. The method of claim 12, comprising forming the flexible biocompatible external tube from an artificial material.

14. The method of claim 12, comprising forming the flexible biocompatible external tube from a natural material.

15. The method of claim 1, comprising implanting the conduit structure for utilization of the multipotent mesenchymal cells for enhancing tissue regeneration in tibial tuberosity advancement.

16. The method of claim 1, comprising implanting the conduit structure for utilization of the multipotent mesenchymal cells for enhancing tissue regeneration in treatment of Perthes disease of the hip.

17. An apparatus to enhance bone regeneration, comprising:
- a first number of segments formed from a material comprising calcium phosphate, at least one of the segments having a first open end configured for ingress of physiological signals proximal to a tissue regeneration site that promote multipotent mesenchymal cell differentiation and egress of mesenchymal cell differentiation products; and
- a second number of segments formed from a material comprising calcium phosphate, at least one of the segments having a second open end immersed in a source of multipotent mesenchymal cells and configured for egress of the physiological signals and ingress of the mesenchymal cell differentiation products;
- wherein the segments directly connect the tissue regeneration site and the source of multipotent mesenchymal cells to form an extravascular or transvascular conduit to enhance the bone regeneration;
- wherein at least one of the first number of segments and at least one of the second number of segments form the conduit having at least a partial opening between the segments for ingress and transit of additional functional cells, cytokines, growth factors, blood, and blood vessels to enhance the bone regeneration;
- wherein the concentration of multipotent mesenchymal cells at the tissue regeneration site is lower than the concentration of multipotent mesenchymal cells at the source of multipotent mesenchymal cells.

18. The apparatus of claim 17, wherein at least one of the first number of segments and at least one of the second number of segments form the conduit from the first open end at the tissue regeneration site to the second open end at an intramedullary bone cavity.

19. The apparatus of claim 17, comprising at least a portion of an inner surface of at least one segment coated with calcium phosphate having a controlled rate of solubility in biological fluids.

20. The apparatus of claim 19, wherein the calcium phosphate of the first number of segments and the second number of segments is selected from a group consisting of tricalcium phosphate, hydroxyapatite, oxyapatite, and fluoroapatite.

21. The apparatus of claim 17, wherein at least one of the first number of segments and the second number of segments is formed from a rigid biocompatible construction comprising a ceramic-to-ceramic composite of a calcium phosphate material for bioactivity and an inert material for strength to reduce damage from external forces.

22. The apparatus of claim 21, wherein the inert material is compatible with the calcium phosphate material in physical properties and chemistry during processing.

23. The apparatus of claim 22, wherein the inert material is a magnesium aluminate spinel.

24. The apparatus of claim 21, wherein at least one of the first number of segments and the second number of segments is an orthopedic implant.

25. A system to enhance tissue regeneration, comprising:
- a number of segments of a conduit having a first open end at a tissue regeneration site to promote physiological signals to transit to a second open end immersed in a histologically rich multipotent mesenchymal cell source, wherein the physiological signals promote differentiation of multipotent mesenchymal cells into tissue regeneration response products that transit the conduit to the tissue regeneration site to enhance the tissue regeneration; and
- a bioactive, biocompatible implant to at least partially fill a void of partitioned bone;
- wherein the concentration of multipotent mesenchymal cells at the tissue regeneration site is lower than the concentration of multipotent mesenchymal cells at the histologically rich multipotent mesenchymal cell source;
- wherein the concentration of physiological signals at the histologically rich multipotent mesenchymal cell source is lower than the concentration of physiological signals at the regeneration site.

26. A system to enhance bone regeneration, comprising:
- a number of conduit segments having a first open end positioned in an intramedullary bone cavity having multipotent mesenchymal cells and/or products thereof;
- the number of conduit segments having a second open end configured for egress of the multipotent mesenchymal cells and/or the products thereof proximal to a site of a partitioned bone; and
- a bioactive, biocompatible implant to at least partially fill a void of the partitioned bone;
- wherein the number of conduit segments and the bioactive, biocompatible implant form a conduit directly connecting the intramedullary bone cavity having the multipotent mesenchymal cells and the site of the partitioned bone to enhance the bone regeneration to fill a remaining void of the partitioned bone with new bone;

wherein the concentration of multipotent mesenchymal cells at the site of a partitioned bone is lower than the concentration of multipotent mesenchymal cells at the intramedullary bone cavity having multipotent mesenchymal cells.

27. The system of claim 26, wherein the bioactive, biocompatible implant has openings that contribute to functionality as a conduit segment.

28. The system of claim 26, wherein the number of conduit segments is formed from an osteoceramic material.

29. The system of claim 26, wherein the second open end of a conduit segment for egress of the multipotent mesenchymal cells and/or the products thereof is configured to substantially match a shape and/or angle of a surface of the partitioned bone proximal to the implant.

30. The system of claim 26, wherein the implant is formed from an osteoceramic material.

31. The system of claim 26, wherein the implant is configured as a wedge to separate a portion of the partitioned bone having an attachment site for a ligament or a tendon from an underlying portion of the partitioned bone.

32. The system of claim 26, wherein the implant is formed from a plurality of segments that are selectable from various shapes and sizes to more effectively fill the void of the partitioned bone.

33. The system of claim 26, wherein the implant is configured to have surfaces that substantially match surfaces of the partitioned bone to reduce a space of the void of the partitioned bone.

34. The system of claim 26, wherein the implant is configured to have a shape and a number of perforations, channels, and/or grooves to guide bone regeneration to fill the void of the partitioned bone with new bone in order to enable the new bone to serve an appropriate bodily function.

35. The system of claim 26, wherein the system comprises a number of cages and/or brackets between opposing surfaces of portions of the partitioned bone configured to maintain an intended separation distance of the portions of the partitioned bone.

36. The system of claim 35, wherein the number of cages and/or brackets are configured to reduce relative movement of the portions of the partitioned bone.

37. An apparatus to enhance bone regeneration, comprising:
a conduit formed from a material comprising calcium phosphate, said conduit having a first open end and a second open end;
wherein the first open end is configured for ingress of physiological signals proximal to a tissue regeneration site that promote multipotent mesenchymal cell differentiation and egress of mesenchymal cell differentiation products; and
wherein the second open end is immersed in a source of multipotent mesenchymal cells and configured for egress of the physiological signals and ingress of the mesenchymal cell differentiation products;
wherein the conduit directly connects the tissue regeneration site and the source of multipotent mesenchymal cells to enhance the bone regeneration;
wherein the concentration of multipotent mesenchymal cells at the tissue regeneration site is lower than the concentration of multipotent mesenchymal cells at the source of multipotent mesenchymal cells;
wherein the concentration of physiological signals at the source of multipotent mesenchymal cells is lower than the concentration of physiological signals at the tissue regeneration site.

38. A method to enhance tissue regeneration during a wound healing and tissue regeneration process, comprising:
placing a conduit having a first end and a second end between a tissue regeneration site having physiological signals at the first end and a multipotent mesenchymal cell site having multipotent mesenchymal cells at the second end;
wherein the physiological signals from the tissue regeneration site induce multipotent mesenchymal cells to create a first type of mesenchymal cell differentiation products at a first time during the wound healing and tissue regeneration process and a second type of mesenchymal cell differentiation products at a second time during the wound healing and tissue regeneration process;
wherein the concentration of multipotent mesenchymal cells at the tissue regeneration site is lower than the concentration of multipotent mesenchymal cells at the multipotent mesenchymal cell site;
promoting the migration of the first type of mesenchymal cell differentiation products and the second type of mesenchymal cell differentiation products to the tissue regeneration site through the conduit.

39. The apparatus of claim 38 wherein the mesenchymal differentiation products are stem cells.

* * * * *